US012676209B2

(12) United States Patent
Haque et al.

(10) Patent No.: US 12,676,209 B2
(45) Date of Patent: Jul. 7, 2026

(54) DESIGNING A PERSONALIZED COMPOSITION FOR COUNTERACTING SKIN MALODOR

(71) Applicant: Tata Consultancy Services Limited, Mumbai (IN)

(72) Inventors: Mohammed Monzoorul Haque, Pune (IN); Sharmila Shekhar Mande, Pune (IN); Swadha Anand, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 658 days.

(21) Appl. No.: 17/985,660

(22) Filed: Nov. 11, 2022

(65) Prior Publication Data

US 2023/0154564 A1 May 18, 2023

(30) Foreign Application Priority Data

Nov. 15, 2021 (IN) .............................. 202121052334

(51) Int. Cl.
| | |
|---|---|
| *G16B 25/10* | (2019.01) |
| *G16B 30/10* | (2019.01) |
| *G16B 45/00* | (2019.01) |
| *G16B 50/30* | (2019.01) |

(52) U.S. Cl.
CPC ............. *G16B 25/10* (2019.02); *G16B 30/10* (2019.02); *G16B 45/00* (2019.02); *G16B 50/30* (2019.02)

(58) Field of Classification Search
CPC ........ G16B 25/10; G16B 30/10; G16B 50/30; G16B 45/00
See application file for complete search history.

(56) References Cited

U.S. PATENT DOCUMENTS 10,169,541 B2    1/2019   Apte et al.
10,633,714 B2    4/2020   Cutcliffe et al.

FOREIGN PATENT DOCUMENTS

WO      WO-2018073276 A1 *   4/2018   .............. A61K 8/99
WO      WO2022168120 A1      8/2022

OTHER PUBLICATIONS

Mcbain et al. 2019 (Consumer Safety Consideration of Skin and Oral Microbiome Perturbation; Clinical Microbiology Reviews 32(4): 1-23) (Year: 2019).*
Mogilnicka et al. 2020 (Microbiota and Malodor—Etiology and Management; International Journal of Molecular Sciences 21(2886) 1-21). (Year: 2020).*

* cited by examiner

*Primary Examiner* — Mary Maille Lyons
(74) *Attorney, Agent, or Firm* — FINNEGAN, HENDERSON, FARABOW, GARRETT & DUNNER LLP

(57) ABSTRACT

This disclosure relates generally to methods and systems for designing a personalized composition that can counteract or reduce skin malodor. Conventional techniques that prepare compositions to treat specific malodorants are limited and such compositions cannot be personalized to an individual according to the type of malodorant produced on skin of the individual. The present disclosure provides a method for designing a personalized composition for degrading the malodorant present in skin of the subject. First, a biological sample from the subject is collected, and metabolite composition of the sample is determined. next, one or more malodorant in the sample are identified based on the metabolite composition. Further, a combination of bacteria capable of degrading the identified malodorant are identified using the microbe-malodorant microbial knowledge base and lastly the personalized composition of the identified bacteria is designed using the combination of bacteria.

2 Claims, 7 Drawing Sheets

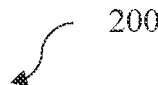

200

Collecting a biological sample of the subject for whom the personalized composition for counteracting skin malodor to be designed   202

Determining a metabolite composition comprising one or more metabolites, from the biological sample, using one or more analytical techniques   204

Identifying one or more malodorants present in the biological sample based on the one or more metabolites present in the determined metabolite composition   206 identifying a combination of one or more microbes, using a microbe-malodorant microbial knowledge base, that (i) have a metabolic capability to degrade the one or more identified malodorants, (ii) possess a capability of colonizing on skin of the subject, and (iii) are not pathogenic to the subject   208

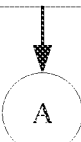

Identifying a subset of pathways using the microbe-malodorant microbial knowledge base, that degrade the one or more identified malodorants 210

Genetically engineering one or more skin-colonizing microbes with the identified subset of pathways, to obtain one or more genetically engineered microbes 212

Designing a personalized composition for counteracting skin malodor of the subject from at least one of (i) the one or more microbes present in the combination of microbes and (ii) the one or more genetically engineered microbes 214

Topically administering the designed personalized composition on the skin of the subject for counteracting skin malodor 216

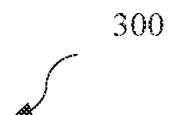

Identifying a plurality of skin metabolites (SM) implicated to be malodorant, from one or more knowledge sources 302

Identifying one or more microbial metabolic pathways that have the capability to degrade at least one of the plurality of skin metabolites, using a literature mining technique, to obtain a plurality of metabolic pathways corresponding to the plurality of skin metabolites, wherein each metabolic pathway comprises genes or enzymes, and a series of chemical reactions for degrading the malodorant 304

Creating a matrix metabolite map (Mmap) having each of the plurality of skin metabolites, the corresponding metabolic pathway and a microbe in which the metabolic pathway is characterized as columns 306

Generating a bacterial genome map (BGM) for each genome listed in a bacterial genome database, wherein the BGM comprises a list of genes for each genome listed in the bacterial genome database and functional annotations for each gene of the list of genes in a form of constituent protein domains identified in each gene, and wherein the list of genes for each genome are arranged as per an order in terms of genomic locations starting from origin of replication 308

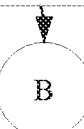

Creating a metabolite pathway-domain map (MPDM) for each of the plurality of skin metabolites using the matrix metabolite map (Mmap), wherein the metabolite pathway-domain map (MPDM) comprises each of the plurality of metabolic pathways associated with the plurality of skin metabolites and a corresponding protein domain 310

Identifying one or more protein domain out of the protein domains present in the metabolite pathway-domain map (MPDM), that are present as gene clusters on each genome listed in the bacterial genome map (BGM) 312

Creating a genome-metabolite-pathway map (GMP) using the metabolic pathway and corresponding genomes 314

Creating a FGmap based on the genome-metabolite-pathway map (GMP) with genera and metabolic pathways 316

Forming the microbe-malodorant bacterial knowledge base by combining the FGmap and the genome-metabolite-pathway map 318

FIG. 3B

Aldehyde dehydrogenation

Aldehydes    ————————————▶    Corresponding acids on
dehydrogenation

Aldehyde
dehydrogenase

FIG. 5

DESIGNING A PERSONALIZED COMPOSITION FOR COUNTERACTING SKIN MALODOR

PRIORITY CLAIM

This U.S. patent application claims priority under 35 U.S.C. § 119 to: Indian Patent Application No. 202121052334, filed on Nov. 15, 2021. The entire contents of the aforementioned application are incorporated herein by reference.

TECHNICAL FIELD

The disclosure herein generally relates to the field of treating or reducing skin malodor, and, more particularly, to methods and systems for designing a personalized composition that can counteract or reduce skin malodor.

BACKGROUND

Various chemicals or metabolites are secreted onto the skin surface by sebaceous, eccrine, and apocrine glands present in the skin of an individual. These chemicals or metabolites do not often have an objectionable odor but may act as nutrients for microbes resident on the skin which transform the chemicals or metabolites to multiple (mal-) odorous compounds (alternately referred as malodorants). Secretions of the apocrine glands in the human axilla comprises or possess precursors which can be metabolized by axillary bacteria and degraded further to products that might lead to axillary malodor. Some experiments showed that metabolites like volatile fatty acids (VFAs) and thioalcohols are associated with axillary malodor. The presence of 16-androstene steroids in axillary secretions has also been implicated in axillary malodor.

Similarly, large number of sweat glands in feet constitutes compounds which can be metabolized by commensal bacteria on the skin of foot to malodor causing chemicals. Foot secretions are primarily attributed to the eccrine sweat glands present on both the plantar and dorsal surface. The main malodorant in feet is isovaleric acid which is generated by enzymatic conversion of Leucine by bacteria.

Most of the existing solutions for treating skin malodor contain antibacterial compounds which inhibit the growth of all skin microbes in a non-specific manner (i.e., they impact or kill both commensal and pathogenic bacteria on skin alike), for example, 2,4,4'-trichloro-2' hydroxy-diphenyl-ether (Triclosan). In addition to killing odor causing bacteria (pathogenic bacteria), the existing solutions lead to destruction of the natural skin microbiome (commensal bacteria) that protects the skin from pathogenic bacteria. This emphasizes the need for methods of removing or counteracting or reducing malodor while preserving skin microbiota in the process. There have been attempts made on treating malodor by degrading specific malodorant. However, conventional techniques that prepare compositions to treat specific malodorants are limited and such compositions cannot be personalized to an individual according to the type of malodorant produced on skin of the individual.

SUMMARY

Embodiments of the present disclosure present technological improvements as solutions to one or more of the above-mentioned technical problems recognized by the inventors in conventional systems.

In an aspect, a method for designing a personalized composition for counteracting skin malodor of a subject is provided. The method including the steps of: collecting a biological sample of the subject for whom the personalized composition for counteracting skin malodor to be designed; determining a metabolite composition comprising one or more metabolites, from the biological sample, using one or more analytical techniques; identifying one or more malodorants present in the biological sample based on the one or more metabolites present in the determined metabolite composition; identifying a combination of one or more microbes, using a microbe-malodorant microbial knowledge base, that (i) have a metabolic capability to degrade the one or more identified malodorants, (ii) possess a capability of colonizing on the skin of the subject, and (iii) are not pathogenic to the subject; identifying a subset of pathways using the microbe-malodorant microbial knowledge base, that degrade the one or more identified malodorants; genetically engineering one or more skin-colonizing and non-pathogenic microbes with the identified subset of pathways, to obtain one or more genetically engineered microbes; designing a personalized composition for counteracting skin malodor of the subject from at least one of (i) the one or more microbes present in the combination of microbes and (ii) the one or more genetically engineered microbes; and topically administering the designed personalized composition on the skin of the subject for counteracting skin malodor.

In another aspect, a system for preparing a personalized composition for counteracting skin malodor of a subject is provided. The system includes a sample collection module; a metabolite identification module; a memory; one or more hardware processors; a microbe-malodorant bacterial knowledge base; an administration module; a malodorant identification module; wherein the one or more hardware processors are configured by the instructions to: collect a biological sample of the subject for whom the personalized composition for counteracting skin malodor to be designed, through the sample collection module; determine metabolite composition comprising one or more metabolites, from the biological sample, using one or more analytical techniques, through the metabolite identification module; identify one or more malodorants present in the biological sample based on the one or more metabolites present in the determined metabolite composition, through a malodorant identification module; identify a combination of one or more microbes, using a microbe-malodorant microbial knowledge base, that (i) have a metabolic capability to degrade the one or more identified malodorants, (ii) possess a capability of colonizing on the skin of the subject, and (iii) are not pathogenic to the subject; identify subset of pathways using the microbe-malodorant microbial knowledge base, that degrade the one or more identified malodorants; genetically engineer one or more skin-colonizing microbes with the identified subset of pathways, to obtain one or more genetically engineered microbes; design a personalized composition for counteracting skin malodor of the subject from at least one of (i) the one or more microbes present in the combination of microbes and (ii) the one or more genetically engineered microbes; and topically administer the personalized composition on the skin of the subject for counteracting skin malodor, through the administration module.

In an embodiment, designing the personalized composition for counteracting skin malodor of the subject from at least one of (i) the one or more microbes present in the combination of microbes and (ii) the one or more genetically engineered microbe, comprises formulating a subset of microorganisms associated with at least one of (i) the one or more microbes present in the combination of microbes and (ii) the one or more genetically engineered microbe, along with at least one of (iii) one or more cosmetically or pharmaceutically acceptable carriers and (iv) one or more cosmetically or pharmaceutically acceptable excipients.

In an embodiment, the microbe-malodorant microbial knowledge base is created by: identifying a plurality of skin metabolites (SM) implicated to be malodorant, from one or more knowledge sources; identifying one or more microbial metabolic pathways that have the capability to degrade at least one of the plurality of skin metabolites, using a literature mining technique, to obtain a plurality of metabolic pathways corresponding to the plurality of skin metabolites, wherein each metabolic pathway comprises genes or enzymes, and a series of chemical reactions for degrading the malodorant; creating a matrix metabolite map (Mmap) having information pertaining to each of the plurality of skin metabolites, the corresponding metabolic pathways, and a microbe in which the metabolic pathway is experimentally characterized; generating a bacterial genome map (BGM) for each genome listed in a bacterial genome database, wherein the BGM comprises a list of genes for each genome listed in the bacterial genome database and functional annotations for each gene of the list of genes in a form of constituent protein domains identified in each gene, and wherein the list of genes for each genome are arranged as per an order in terms of genomic locations starting from origin of replication; creating a metabolite pathway-domain map (MPDM) for each of the plurality of skin metabolites using the matrix metabolite map (Mmap), wherein the metabolite pathway-domain map (MPDM) comprises each of the plurality of metabolic pathways associated with the plurality of skin metabolites and a corresponding protein domain; identifying one or more protein domain out of the protein domains present in the metabolite pathway-domain map (MPDM), that are present as gene clusters on each genome listed in the bacterial genome map (BGM); creating a genome-metabolite-pathway map (GMP) using the metabolic pathway and corresponding genomes; creating a FGmap based on the genome-metabolite-pathway map (GMP) with genera and metabolic pathways; and forming the microbe-malodorant bacterial knowledge base by combining the FGmap and the genome-metabolite-pathway map (GMP).

In an embodiment, identifying the combination of one or more microbes, using the microbe-malodorant microbial knowledge base, that (i) have the metabolic capability to degrade the one or more identified malodorants, (ii) possess the capability of colonizing on the skin of the subject, and (iii) are not pathogenic to the subject, comprises: parsing the one or more malodorants through a FGmap and a genome-metabolite-pathway map (GMP) of the microbe-malodorant microbial knowledge base.

In an embodiment, the personalized composition for counteracting skin malodor of a subject, is in the form of a lotion, cream, ointment, aerosol spray, mist, oil, or gel.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIGS. 2A and 2B is a flowchart illustrating a method for designing the personalized composition for counteracting skin malodor of the subject, according to some embodiments of the present disclosure.

FIGS. 3A and 3B collectively referred as FIG. 3 is a flowchart illustrating process of creating a microbe-malodorant microbial knowledge base for designing the personalized composition for counteracting skin malodor of the subject by the method illustrated in FIGS. 2A and 2B, according to some embodiments of the present disclosure.

FIG. 5 illustrates the exemplary metabolic pathway for degrading aldehydes, according to some embodiments of the present disclosure.

DETAILED DESCRIPTION

Figure 1:
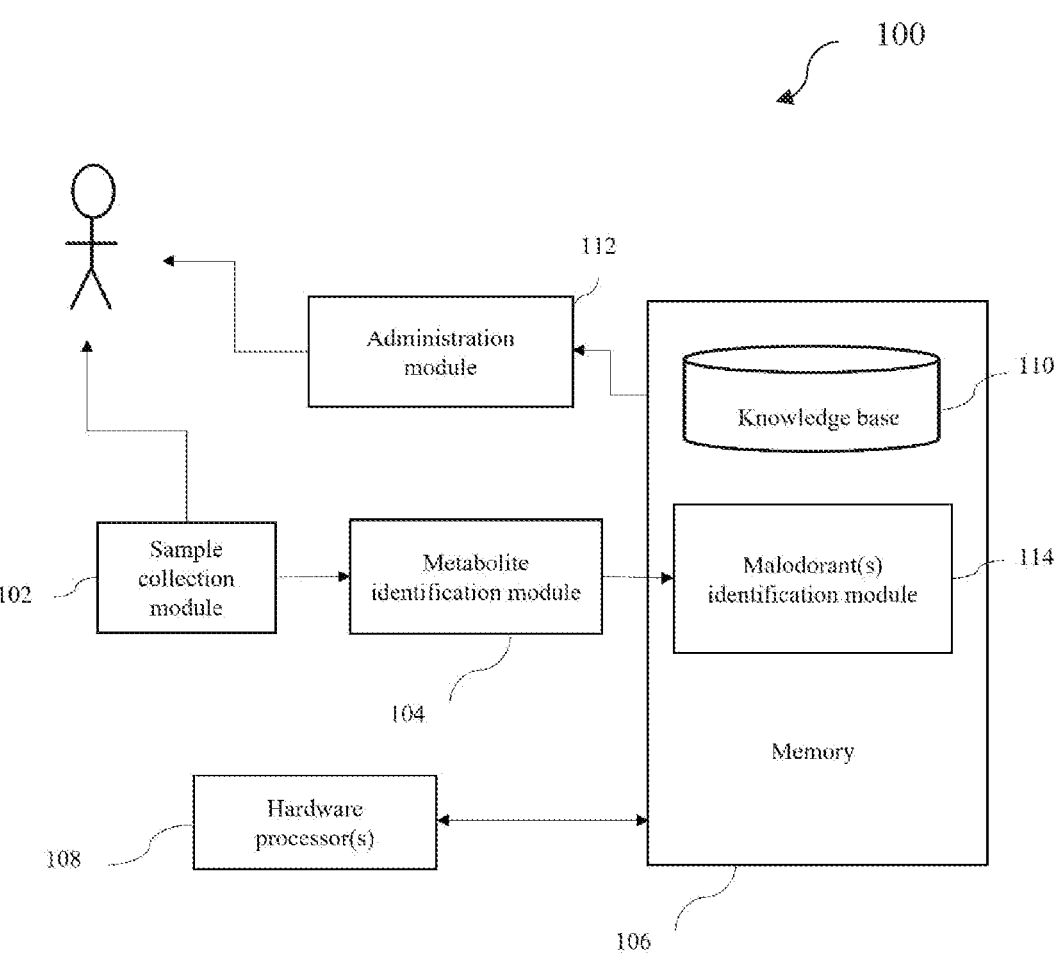
FIG. 1 illustrates an exemplary system for designing a personalized composition for counteracting skin malodor of a subject, according to some embodiments of the present disclosure.
Figure 4:
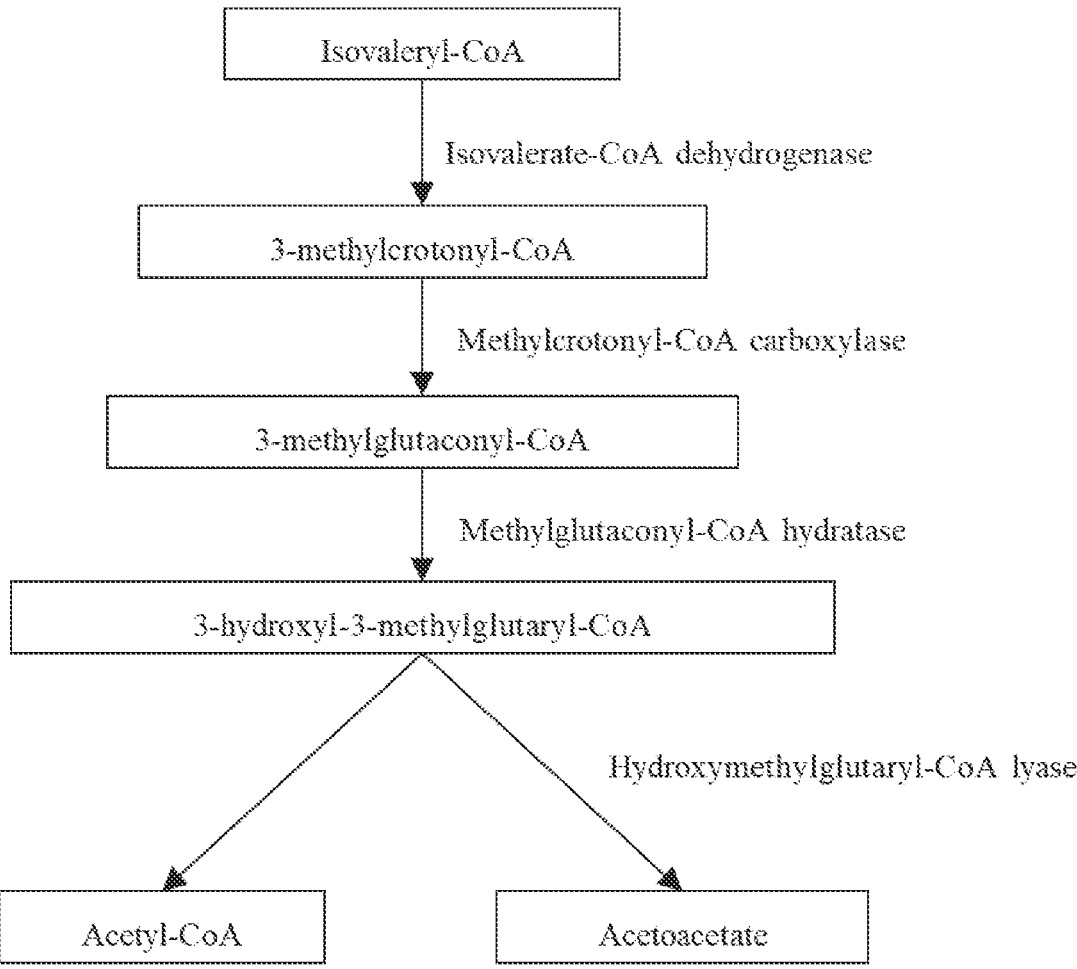
FIG. 4 illustrates an exemplary metabolic pathway for degrading isovalerate, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Certain glands on human skin (usually in axilla and feet) produce compounds which are degraded by bacteria to produce certain malodorant resulting in foul smell. Owing to the similarity in foot and axillary malodor, the term malodorant in present disclosure refers to odorous compounds that cause foot or axillary malodor. Existing techniques of treating malodor either inhibit the growth of skin microbes in a non-specific manner or treat only specific type of malodorant. Hence, there is a need for a method of designing a composition for treating a skin malodor and are personalized to a subject or an individual. The compositions should also not harm any useful skin microbes.

Embodiments of present disclosure provide a method for designing a personalized composition comprising one or more microbes that are non-pathogenic, can colonize on the skin of the subject, and degrade the malodorant present in skin of the subject (alternatively referred as the individual or a person). As a precursor step, a microbe-malodorant microbial knowledge base is created which comprises metabolites responsible for the skin odor and corresponding metabolic pathways in microbes for their degradation. This is a one-time activity. For treating malodor in the individual, skin swab/scrape sample from the individual is collected, and metabolite composition of the collected sample is determined. Further, one or more malodorant in the sample are identified based on the metabolite composition. Further, a combination of one or more bacteria capable of degrading one or more identified malodorant(s) is identified using the microbe-malodorant microbial knowledge base and the personalized composition (alternately referred as formulation or microbial cocktail herein) of the identified bacteria is created and topically administered to the individual for treating skin malodor.

Referring now to the drawings, and more particularly to FIG. 1 through 5, where similar reference characters denote corresponding features consistently throughout the figures, there are shown preferred embodiments and these embodiments are described in the context of the following exemplary system and/or method.

FIG. 1 illustrates an exemplary system (100) for designing the personalized composition for counteracting skin malodor of the subject, according to some embodiments of the present disclosure. In an embodiment, the system 100 includes of a sample collection module 102, a metabolite identification module 104, a memory 106, one or more hardware processors 108, a microbe-malodorant bacterial knowledge base 110, an administration module 112, and a malodorant identification module 114 as shown in FIG. 1. The one or more hardware processors 108 are in communication with the memory 106. In an embodiment, the malodorant identification module 114 and the microbe-malodorant bacterial knowledge base 110 are stored in the memory 106.

The microbe-malodorant bacterial knowledge base 110 stores information including metabolites responsible for skin odor and corresponding metabolic pathways in the microbes for their degradation. The one or more hardware processors 108 (referred as processors, herein after) can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory 106.

The memory 106 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. Functions of the components of system 100 are explained in conjunction with flow diagrams depicted in FIGS. 2 and 3 for designing the personalized composition for counteracting skin malodor of the subject.

In an embodiment, the memory 106 comprises one or more data storage devices operatively coupled to the processor(s) 108 and is configured to store instructions for execution of steps of the method depicted in FIGS. 2A and 2B and FIG. 3 by the processors 108. The steps of the method of the present disclosure will now be explained with reference to the components or blocks of the system 100 as depicted in FIG. 1 and the steps of flow diagrams as depicted in FIGS. 2A and 2B and FIG. 3. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

FIGS. 2A and 2B is a flowchart illustrating a method 200 for designing the personalized composition for counteracting skin malodor of the subject, according to some embodiments of the present disclosure. At step 202 of the method 200, a biological sample (for example, a skin swab sample) is collected from the subject for whom the personalized composition for counteracting skin malodor to be designed, through the sample collection module 102. In an embodiment, the subject or the individual is a human being. In an embodiment, the biological sample (for example, the skin swab sample) is collected from skin or subcutaneous tissue of the subject by non-invasive methods including, but not limited to, tape stripping, scraping, swabbing, or invasive techniques such as biopsy of an individual.

In another embodiment, the biological sample is collected from clothing of the subject used to cover areas on the skin where malodorant are to be detected. For example, foot odorants can be obtained by wearing pre-ether-extracted socks (synthetic fiber) which can be followed by physical exercise. Feet extracts can be obtained from socks using ethyl ether which can evaporate to provide a dried sample. In another example, sweat samples can be collected by people wearing a sterilized plastic bag and subjected to physical exercise so that the sweat can be collected and extracted. With reference to the disclosure described herein, skin, and subcutaneous tissue refer to the epidermis, the underlying dermis, as well as secretory glands on skin including sweat and sebaceous glands as understood by a person skilled in the art. Throughout the present disclosure, "cutaneous", "subcutaneous" and "skin" can be used interchangeably to refer to a skin surface on which the presence of certain metabolites may influence malodor generation.

Further, at step 204 of the method 200, a metabolite composition of the collected biological sample is determined using one or more analytical techniques. The metabolite composition comprised one or more metabolites present in the collected biological sample at step 202 of the method 200. The metabolite identification module 104 is used to determine the metabolite composition of the collected biological sample. The metabolite identification module 104 further includes DNA extraction techniques, mass spectrometry, and so on. In an embodiment, the metabolite composition is determined by isolating nucleic acid molecules present in the biological sample and performing nucleic acid analysis or protein analysis by the DNA extraction technique. In an embodiment, the nucleic acid molecules include deoxyribonucleic acid (DNA), and Ribonucleic acid (RNA). In one embodiment, mini-DNA extraction kits may be utilized for extraction of the DNA. The metabolite composition of the biological sample can be determined by using the nucleic acid or protein analysis.

In an embodiment, the nucleic acid analysis involves analyzing DNA, RNA, mRNA, rRNA using techniques including, but not limited to, a Polymerase Chain Reaction (PCR), a quantitative polymerase chain reaction (qPCR), pyrosequencing, Denaturing gradient gel electrophoresis (DGGE), Restriction Fragment Length Polymorphism, microarrays, or next generation sequences. Any other techniques capable of detecting nucleic acid sequences or DNA hybridization are within the scope of the present disclosure. In an embodiment, the protein analysis is carried out using techniques including, but not limited to, Gel Electrophoresis, Mass spectroscopy, AQUA, iTRAQ etc. Any other techniques of determining presence of proteins that can be used as indicators of presence of specific bacteria is within the scope of this disclosure. In an embodiment, any other laboratory acceptable techniques for nucleic acid and protein analysis can also be utilized to determine the metabolite composition of the collected biological sample.

Further at step 206 of the method 200, one or more malodorant present in the biological sample, are identified based on the metabolite composition determined at step 204 of the method 200, through the malodorant identification module 114. One of conventional analytical techniques is used to identify the one or more malodorant present in the biological sample. In an embodiment, the conventional analytical techniques including but not limited to solid phase microextraction gas chromatography mass spectrometry (SPME-GC-MS), high-resolution GC-MS, GC-Fourier transform infrared spectroscopy (GC-FTIR), thermal desorption GC-MS, cavity ringdown spectroscopy (CRDS), high-performance liquid chromatography (HPLC), selected ion flow tube (SIFT)-MS, proton transfer reaction mass spectrometry (PTR-MS) electrospray tandem-mass spectrometry, liquid chromatography-tandem mass spectrometry (LC-TMS), selective reagent ionization time-of-flight mass spectrometry (SRI-TOF-MS) and ion mobility spectrometry (IMS) etc. Any other techniques of identifying metabolites in skin samples such as but not limited to spectrometric, fluorometric, chromatographic, enzyme assay, chemical assay etc. are within the scope of this disclosure.

In an embodiment, the one or more malodorants include volatile short and medium chain fatty acids such as valeric acid, isovaleric acid, acetic acid, propionic acid, and so on. In another embodiment, the one or more malodorants include one or more of Hydrogen Sulfide and ammonia. In another embodiment, the one or more malodorants may also comprise thioalcohols and steroid compounds. Any other compounds capable of producing offensive malodor is within the scope of the present disclosure.

Further at step 208 of the method 200, the processor 108 is configured to identify a combination of one or more microbes based on the one or more malodorants identified at step 206 of the method 200. The combination of one or more microbes are identified in such a way that they (i) have a metabolic capability to degrade the one or more identified malodorants, (ii) possess a capability of colonizing on the skin of the subject, and (iii) are not pathogenic to the subject. In an embodiment, the one or more microbes are co-culturable microbes. The microbe-malodorant microbial knowledge base 110 is used to identify the combination of one or more microbes based on the one or more malodorants identified at step 206 of the method 200.

In an embodiment, the combination of one or more microbes are identified by parsing the one or more malodorants, through FGmap and Gmap of the microbe-malodorant microbial knowledge base 110, by the processors 108 using the instructions and executable programs stored in the memory 106. In an embodiment, the combination of one or more microbes are the bacteria (live bacterial strains) and comprise one or more of bacterial strains with the required metabolic repertoire for degradation of one or more malodorants and belonging to genera comprising one or more of but not limited to:

(i) bacterial strains for degradation of isovalerate: *Acidovorax, Acinetobacter, Aeribacillus, Aeromonas, Agrobacterium, Alicycliphilus, Alicyclobacillus, Alteromonas, Anoxybacillus, Antarctobacter, Aquaspirillum, Asticcacaulis, Aureimonas, Azoarcus, Azospirillum, Azotobacter, Bacillus,* Bacterioplanes, *Bdellovibrio, Bradyrhizobium, Brevibacillus, Brucella, Burkholderia, Candidatus, Colwellia,* Comamonadaceae, *Comamonas, Corynebacterium, Cycloclasticus, Dechloromonas,* Defluviimonas, *Delftia, Dinoroseobacter, Dyella, Ensifer, Ferrimonas, Geobacillus, Geobacter, Glaciecola, Hahella,* Halioglobus, *Halobacillus, Halomonas, Hydrogenophaga, Jannaschia, Janthinobacterium, Kangiella, Labrenzia,* Lacimicrobium, *Legion-*

*ella, Leisingera, Leptothrix, Limnohabitans, Loktanella,* Luteitalea, *Lysinibacillus, Lysobacter, Magnetospirillum, Marichromatium, Marinobacter, Marinobacterium, Marinomonas, Marinovum,* Marivivens, *Martelella, Massilia, Methylibium, Methylocystis, Mica vibrio, Microbulbifer, Moraxella, Moritella,* Neorhizobium, *Niabella,* Nitrospirillum, Oblitimonas, Oceanicoccus, *Ochrobactrum, Octadecabacter, Oleiphilus, Pandoraea, Pannonibacter,* Paraburkholderia, *Paracoccus,* Parageobacillus, Pararhodospirillum, *Pelagibaca, Phaeobacter,* Planktomarina, *Polaromonas, Polyangium,* Polymorphum, *Pseudoalteromonas, Pseudogulbenkiania,* Pseudohongiella, *Pseudomonas, Pseudoxanthomonas, Psychrobacter, Ralstonia, Ramlibacter, Rhizobacter,* Rhizobiales, *Rhizobium, Rhodobacter, Rhodococcus, Rhodoferax, Rhodospirillum, Rhodovulum, Roseateles, Roseibacterium, Roseobacter, Roseomonas, Roseovarius, Ruegeria,* Rugosibacter, *Rummeliibacillus, Salimicrobium, Shewanella, Shinella, Simiduia, Sinorhizobium, Sporosarcina, Sulfitobacter, Sulfuritalea, Tatlockia, Thalassospira, Thauera,* Thiobacimonas, *Thioclava, Thiomonas, Tumebacillus, Variovorax, Vibrio, Virgibacillus, Vitreoscilla, Xanthobacter, Xanthomonas;*

(ii) Bacterial strains for degradation of nonenal: *Acetobacter, Acidovorax, Advenella, Aeromonas, Agrobacterium, Alcaligenes, Alcanivorax, Altererythrobacter, Antarctobacter, Aureimonas, Azorhizobium, Azospirillum, Beijerinckia, Belliella, beta,* Betaproteobacteria, *Bordetella, Bosea, Bradyrhizobium, Burkholderia, Candidatus, Caulobacter, Chelativorans, Chelatococcus, Collimonas, Comamonas, Cupriavidus, Delftia, Desulfovibrio, Desulfuromonas, Devosia, Dinoroseobacter, Dokdonella, Dyella, Emticicia, Erwinia, Fibrella,* Flammeovirgaceae, *Frateuria, Gluconacetobacter, Gluconobacter, Granulibacter, Granulosicoccus, Halomonas, Herbaspirillum, Hydrogenobacter, Hyphomicrobium, Hyphomonas, Janthinobacterium, Komagataeibacter, Kozakia, Leadbetterella, Leptothrix, Limnohabitans, Luteibacter,* Luteitalea, *Lysobacter, Marinobacterium,* Marivivens, *Martelella, Mesorhizobium, Methylobacterium, Methylocella, Mucilaginibacter,* Neoasaia, Neorhizobium, *Niastella, Nitrobacter,* Nitrospirillum, *Novosphingobium, Oleispira, Opitutus, Paenalcaligenes, Pandoraea, Pannonibacter, Pantoea,* Paraburkholderia, *Paracoccus, Phaeobacter, Planctomyces, Polaromonas, Polynucleobacter, Pragia, Providencia, Pseudomonas,* Pseudorhodoplanes, *Psychromonas, Ralstonia, Ramlibacter, Rhizobium, Rhodobacter, Rhodoplanes, Rhodopseudomonas, Rhodovulum, Robiginitalea, Roseateles, Ruegeria, Serratia, Shewanella, Shimwellia, Sinorhizobium, Sphingobacterium, Sphingomonas, Starkeya, Sulfitobacter, Tateyamaria, Tatumella, Terriglobus,* Thiobacimonas, *Tistrella, Variovorax, Xanthobacter*

(iii) Bacterial strains for degradation of Hydrogen sulfide: *Achromobacter, Acidiphilium, Advenella, Agrobacterium, Anaeromyxobacter, Antarctobacter, Arcobacter, Azospirillum, beta, Beta* proteobacteria, *Bosea, Bradyrhizobium, Candidatus, Celeribacter, Comamonas,* Con fluentimicrobium, *Cupriavidus, Dechloromonas,* Defluviimonas, *Dinoroseobacter, Halomonas, Herminiimonas, Hoeflea, Hydrogenophaga, Hyphomicrobium, Janthinobacterium, Labrenzia, Leisingera, Leptothrix, Limnohabitans, Marinobacter, Marinovum,* Marivivens, *Meiothermus, Mesorhizobium, Methylibium,*

*Methylobacterium, Methyloversatilis, Nitratifractor, Octadecabacter, Oligotropha, Pandoraea, Paracoccus, Pelagibaca, Phaeobacter,* Planktomarina, *Polaromonas, Polymorphum, Polynucleobacter,* Pseudorhodoplanes, *Ralstonia, Ramlibacter, Rhizobium, Rhodobacter, Rhodoferax, Rhodopseudomonas, Rhodovulum, Roseibacterium, Roseobacter, Roseovarius, Ruegeria, Starkeya, Sulfurimonas, Sulfurospirillum, Sulfurovum, Thauera, Thermus,* Thiobacimonas, *Thioclava, Thiomonas, Vitreoscilla, Xanthobacter, Yangia*

Further, at step 210 of the method 200, a subset of pathways is identified using the microbe-malodorant microbial knowledge base 100, that can degrade the one or more identified malodorants identified at step 206 of the method 200. In an embodiment, the subset of pathways is identified by parsing the one or more identified malodorants, through a FGmap and a GMP of the microbe-malodorant microbial knowledge base 110, by the processors 108 using the instructions and executable programs stored in the memory 106.

Further, at step 212 of the method 200, one or more genetically engineered microbes are obtained by genetically engineering one or more skin-colonizing microbes with the identified subset of pathways at step 210 of the method 200. In an embodiment, commensal/symbiont bacteria in skin are transformed using laboratory accepted recombinant DNA techniques to insert genetic machinery capable of degradation/modification of malodorant into the engineered bacteria. The expression of the genetic machinery can be regulated by using specific promoters as well as transcription factor binding sites as part of the construct. In another embodiment, the skin commensal/symbiont bacteria are grown under selective pressure to acquire or lose a gene, gene product, or expression thereof comprising of genes involved in degradation of an odorant. In a certain embodiment, the bacteria are transformed using a Clustered Regularly Interspaced Short Palindromic Repeats (CRISPR) technology to insert genes forming a metabolic pathway for degradation of an odorant. In a certain embodiment, the bacteria are transformed using homologous recombination to acquire genes forming the metabolic pathway for degradation of an odorant.

In one embodiment, the present disclosure provides a modified or engineered microorganism, wherein the organism expresses heterologous one or more of pathways required to degrade odorant metabolites. In some embodiments these pathways may include genes involved in degradation of odorants like isovaleric acid, thioalcohols, nonenal and other aldehydes etc. The metabolic pathways for degradation of other odorant metabolites are also in the scope of this disclosure. A "modified" or "engineered" microorganism refers to a microorganism capable of surviving on skin as a commensal or a symbiont whose naturally occurring form has been changed, such as having been engineered to express a heterologous metabolic pathway.

A "heterologous" protein or a pathway refers to a gene or a set of genes forming a pathway and catalyzing a metabolic reaction or a series of metabolic reactions which are not normally encoded by the genome of the microorganism. Accordingly, heterologous production of proteins forming a pathway involves introducing/inserting a DNA sequence encoding genes/set of genes corresponding to a particular pathway into the microorganism along with a promoter and terminator sequence capable of operating in the said microorganism. The proteins forming a pathway can be expressed using a suitable expression vector or other construct introduced into the microorganism. The suitable vector might comprise of other genetic machinery as is known in the art for successful genetic engineering of target commensal/symbiont bacteria. The heterologous pathway is introduced into the modified organism encoded by a plasmid or on DNA segment which is introduced into the bacterial chromosome.

In an embodiment, the commensal/symbiont bacteria that can be genetically engineered to possess the genetic repertoire for degradation of odorants include residents of skin microbiome at different body sites like *Staphylococcus epidermidis* and other coagulase-negative staphylococci, coryneform of the phylum Actinobacteria like the genera *Corynebacterium, Propionibacterium* and *Brevibacterium* and the genus *Micrococcus* or genus *Propionibacterium*. Any other bacteria capable of residing in different skin sites can be utilized for modification. In another embodiment, one or more probiotic microorganisms especially of the *Lactobacillus* and/or *Bifidobacterium* genera can be genetically engineered. In other embodiments, microorganisms suitable for engineering the pathways for degradation of odorant compounds may also include one or more of bacteria of genera *Bacteroides, Fusobacterium, Melissococcus, Enterococcus, Lactococcus, Bacillus, Pediococcus, Micrococcus, Leuconostoc, Weissella, Aerococcus,* Oenococcus, and mixtures thereof. In other embodiments, methods of gene editing including but not limited to CRISPR-Cas, TALENs, meganucleases and/or Cpf1 systems are used to modify certain gram-negative bacteria found on skin including those belonging to genera *Acinetobacter, Klebsiella* etc. by removing genes encoding for virulence factors as well as other genes responsible for pathogenicity of the microbe. In other embodiments the odorant degradation metabolic pathways can be engineered in organisms that exist as commensals on skin like commensal strains of genera *Micrococcus, Staphylococcus, Corynebacterium* etc.

Further, at step 214 of the method 200, the personalized composition for counteracting skin malodor of the subject is designed from at least one of (i) the one or more microbes present in the combination of microbes identified at step 208 of the method 200 and (ii) the one or more genetically engineered microbes obtained at step 212 of the method 200. In an embodiment, the personalized composition is designed only from the one or more microbes present in the combination of microbes identified at step 208 of the method 200. In another embodiment, the personalized composition is designed only from) the one or more genetically engineered microbes obtained at step 212 of the method 200.

Yet in another embodiment, the personalized composition is designed using the one or more microbes present in the combination of microbes and the one or more genetically engineered microbes. In an embodiment, the one or more microbes present in the combination of microbes and the one or more genetically engineered microbes, are selected while designing the personalized composition, based on the availability of such microbes that (i) have the metabolic capability to degrade the one or more identified malodorants, (ii) possess the capability of colonizing on the skin of the subject, and (iii) are not pathogenic to the subject.

The personalized composition comprising the combination of bacteria for counteracting or reducing malodor in the skin of the subject. In an embodiment, the personalized composition comprises microbes (or combination of bacteria) which helps in degradation of malodorant released by microbes on the skin of the individual. In another embodiment the personalized composition comprises live bacterial strains which contain the genes/proteins/enzymes forming metabolic pathways which can degrade odorant compounds or metabolites.

In an embodiment, the personalized composition for counteracting skin malodor of the subject is designed by formulating a subset of microorganisms associated with at least one of (i) the one or more microbes present in the combination of microbes and (ii) the one or more genetically engineered microbe. Further, the personalized composition is designed along with at least one of (i) one or more cosmetically or pharmaceutically acceptable carriers and (ii) one or more cosmetically or pharmaceutically acceptable excipients.

Further, at step 216 of the method 200, the personalized composition designed at step 214 of the method 200, is topically administered on the skin of the subject for counteracting skin malodor, through the by the administration module 112. In an embodiment, the personalized composition is designed in one of the form from a list including but are not limited to a lotion, ointment, aerosol spray, mist, oil, or gel adapted to be rubbed onto the skin. The personalized composition may also be administered in the form of consumer products including but not limited to skin care products (e.g., bath preparations, foot care products, skin cosmetics etc.), scalp and hair care products (oils, shampoos, conditioners etc.) as well as products like sunscreens, deodorants, shaving creams, fragrances etc.). The personalized composition may be applied in the form of a cosmetic mask preparation or cosmetic strip to remove odor causing substances.

In an embodiment, effect of the personalized composition designed by the method 200 can be tested by laboratory experiments. Before administering the personalized composition, skin malodor in a person is detected using sniffing the nose analysis, preferably the nose of a skilled person. The odor density is then categorized on a scale of 0-10. Preferably these categories may be defined as: 0-3 (no to slight odor detectable), 4-7 (detectable odor) and 8-10 (strong odor). In an embodiment, detection may be carried out by panel of persons trained or not having training in detecting the odor. In another embodiment, a panel of 3 persons can provide independent categories for the odor and the value considered for the odor can be calculated.

The mean or median values for the categories of odor provided by the panel can be considered as odor intensity. In another embodiment, malodorant in an individual can be obtained either by comparing with a database of reference value of skin metabolome profiles of healthy individuals with no malodor or within two samples obtained from the same individual. The individuals with no malodor refer to those whose odor intensity determined by sniffing the nose analysis is in the range 0-3. The individuals with malodor category detected in the range 4-7 are considered to create a database for mild odor while those with a range of 7-10 for malodor category are included as reference for strong odor.

The reference values for no malodor individuals are defined as a numerical range for each metabolite observed in these individuals. The reference values for mild malodor individuals are defined as a numerical range for each metabolite in which it is expected to be found in the individuals assigned to this category. The reference values for strong malodor individuals are defined as a numerical range for each metabolite in which it is expected to be found in these individuals. In an embodiment, a reference database can be created using metabolite composition from skin samples of different categories of odor. The metabolite profile of the individual whose odorants are being tested for can be matched to the reference values for each metabolite. The metabolite level statistically different from the metabolite ranges of no/slight odor category in the database and lying within the metabolic ranges for mild to strong odor category can be shortlisted as odorants causing malodor in an individual.

In another embodiment, a skin sample of an individual can be obtained in conditions like immediately after a bath or in a comfortable environment devoid of sweat secretions etc. can be obtained. A second sample can be obtained from the same individual after changing environment to induce secretions like physical exercise or moving into a hot environment. The metabolite levels can be compared in both these samples and the metabolites showing a predefined fold change between two samples can be considered as odorants in an individual. In an embodiment the fold change can be greater than or equal to 1.5. Similarly, odor intensity of the individual after administering the composition is determined and compared with the odor intensity determined before administering the composition to identify the effect of the composition in counteracting malodor. If the individual's odor intensity falls within reference range of odor in category 7-10 before administering the composition, then a reduction refers to odor values corresponding to range 4-7 after administering the composition. An elimination of an odor will refer to category range 0-3 for malodor. Similarly, for an individual where odor lies in the range 4-7, a reduction/elimination will refer to odor values corresponding to range of odor 0-3.

FIGS. 3A and 3B collectively referred as FIG. 3 is a flowchart illustrating process 300 of creating the microbe-malodorant microbial knowledge base for designing the personalized composition for counteracting skin malodor of the subject by the method 200 illustrated in FIGS. 2A and 2B, according to some embodiments of the present disclosure. At step 302 of the process 300, the processors 108 are configured to identify a plurality of skin metabolites (SM) implicated to be malodorant (OM), using one or more knowledge sources. In an embodiment, the one or more knowledge sources are knowledge databases that are created using a querying technique over the existing literature of skin metabolites and their capability as malodorants. In an embodiment, patent and non-patent literature databases are used as the existing literature. In an embodiment, a query string is used as input to search against non-patent literature databases. An example query strings is: 'Skin Malodor' or 'Malodor+Metabolites' or 'Metabolite name+skin malodor'.

Further, at step 304 of the process 300, the processors 108 are configured to identify one or more microbial metabolic pathways (PiSM) that have the capability to degrade at least one of the plurality of skin metabolites by using literature mining techniques. A plurality of metabolic pathways corresponding to the plurality of skin metabolites are obtained. Each metabolic pathway comprises genes or enzymes and a series of chemical reactions for degrading thee malodorant. The genes comprising a metabolic pathway (PiSM) might have homologs in various other pathways within the same bacterial genome. Therefore, it is important to differentiate the homolog involved in PiSM, also termed from now on as cognate homolog, from its other homologs.

In an embodiment, genes encoding protein or enzymes which function as a pathway and are involved in degradation or formation, or metabolism of a compound often occur in juxtaposed positions on the bacterial genome and these genes are together termed as operons or gene clusters. The occurrence of genes encoding metabolic pathways in gene clusters can be utilized to identify the cognate homolog belonging to the pathway from its other homologs on the genome. A query string Q is used as input for metabolite to search against non-patent literature databases or pathway repositories or any patent literature search engine. An example query string is: ['NameString']+[Gene cluster OR operon]+[Microbe] where NameString=(OM)+[Degradation OR Biosynthesis OR Metabolism]. The result set obtained from literature search in these databases provides the list of abstracts (AO) corresponding to each journal publication as output along with a list of organisms (OO) in which the pathway is experimentally characterized.

Use of any other databases for obtaining pathway and gene information for metabolism of different metabolites as well results of literature mining in any other format are within scope of the disclosure. In one embodiment, the formats for results of literature mining can be one or more from full publication, review article, online information, book articles etc. Further, a manual search of the pathway(s) for metabolite OM degradation/biosynthesis (which is a series of steps or chemical reactions of degradation/biosynthesis of candidate metabolite encoded by the genes on a bacterial genome) and the genes/enzymes involved in the process.

Further, at step 306 of process 300, the processors 108 are configured to create a matrix metabolite map (Mmap) having the information pertaining to each of the plurality of skin metabolites, and the corresponding metabolic pathways, and the microbe (organisms) in which the metabolic pathway is experimentally characterized. An example scenario of a prototype table for Mmap is shown as in Table 1.

TABLE 1

| Metabolite | Pathway | Degradation/ Biosynthesis/ Metabolism | List of Organisms obtained from literature |
|---|---|---|---|
| M1 | P1 | Degradation | O1, O2, O3 |
| M2 | P3 | Biosynthesis | O4, O5 |
| M3 | P4 | Degradation | O7, O8, O10 |
| M4 | P7 | Metabolism | O9, O11, O19 |
| . . . | . . . | . . . | . . . |

Figure 5:
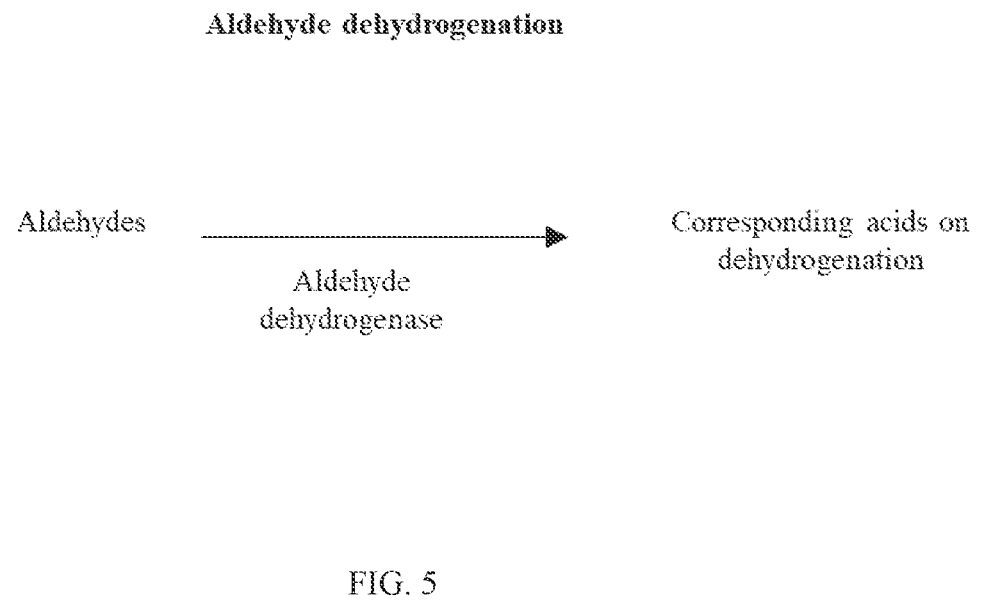

In an embodiment, the malodorant is isovalerate. The pathway for degradation of isovalerate comprises of liu gene cluster in bacterial genomes which brings about degradation of Leucine/Isovalerate to acetate. The reactions as well as genes/enzymes involved in the degradation pathway have been illustrated in FIG. 4. In another embodiment, aldehydes on the skin like hexanal, pentanal, heptanal, octanal, nonanal, decanal, nonenal, benzaldehyde etc. are identified as malodorant and broad-spectrum aldehyde dehydrogenases can be utilized to convert them to corresponding carboxylic acids as illustrated in FIG. 5. In another embodiment, hydrogen sulfide can be identified as an malodorant which can be oxidized by Sulphur oxidizing bacteria where the metabolic pathway comprises Sox gene cluster which is well studied in the art. In another embodiment, thioalcohols can be responsible for skin malodor and pathways for their degradation are identified. Any other metabolites responsible for generation of odor on skin as well as pathways to degrade them is in the scope of present disclosure.

Ammonia oxidation pathway: Oxidation of Ammonia releases Nitrate through a three-step process. The enzyme Ammonia monooxygenase (Amo, EC 1.14, 99.39) catalyzes the conversion of Ammonia to Hydroxlamine, which is then converted to Nitrite by hydroxylamine dehydrogenase (Hao, EC 1.7.2.6). Nitrite further is metabolized to Nitrate by nitrate reductase (EC 1.7.5.1). In an alternate process, oxidation of Ammonia produces Carbamoyl phosphate by the enzyme carbamoyl-phosphate synthase (EC 6.3.4.16).

Ammonia oxidation pathway has been referred to as 'beneficial pathway' throughout the specification.

Isovalerate degradation: Isovalerate degradation begins with isovalerate-CoA dehydrogenase (EC 1.3.8.4) which converts it to 3-Methylcrotonyl-CoA. The next step is catalyzed by Methylcrotonyl-CoA carboxylase (EC 6.4.1.4) and leads to formation of 3-Methylglutaconyl-CoA. This is followed by 3-Methylglutaconyl-CoA hydratase (EC 4.2.1.18) which converts it to Hydroxymethylglutaryl-CoA. Further Hydroxymethylglutaryl-CoA lyase (EC 4.1.3.4) leads to production of acetoacetate and Acetyl-CoA.

Aldehyde degradation: One of the major categories of malodorants in human body are aldehydes produced by axillary-resident bacteria. Aldehyde degradation can be achieved by a combination of enzymes in the category aldehyde dehydrogenase (EC 1.2.1) and alcohol dehydrogenases (EC number 1.1.1).

Urea degradation: Urea degradation in bacteria is brought about by urease (EC 3.5.1.5) gene cluster ureABCEFGD. The $\alpha$, $\beta$, and $\gamma$ subunits form the apoenzyme and are encoded by genes ureA, ureB, and ureC, whereas ureEFGD genes form the accessory proteins for the catalytic enzyme.

Further, at step 308 of the process 300, the processors 108 are configured to generate a bacterial genome map (BGM) for each genome listed in a bacterial genome database (BGD). The BGM includes a list of genes for each genome listed in the bacterial genome database and functional annotations for each gene of the list of genes in a form of constituent protein domains identified in each gene. The list of genes for each genome are arranged as per an order in terms of genomic locations starting from origin of replication In an embodiment, information is obtained for each bacterial genome pertaining to its translated protein sequences for each gene and its location on the bacterial genomes from the repository National Centre of Biotechnology Information (NCBI). The database of the bacteria (strain names) for which the genomes were used in analysis is termed as the Bacterial Genome Database (BGD). The protein sequences are utilized in FASTA format and the feature files in NCBI repository are utilized to ascertain the gene locations, while any other format or source of gene locations and protein sequences for microbial genomes is within scope of disclosure. These bacterial genomes are functionally annotated to identify protein domains within each gene on the genome using multiple methods which may include but are not limited to gene homology (BLAST etc.), Hidden Markov Model based identification (Protein Family or PFAM Database etc.), Position Specific Scoring matrices (PSSM), SMART database etc.

In one embodiment, the database PfamDB (or protein domain family database) comprising HMMs corresponding to all protein domains can be obtained as taught in PFAM database and the genomes can be searched using publicly available software like HMMER. The use of any other protein domain identification method or functional protein annotation method or database or structure-based protein identification method is also well within the scope of this disclosure. The list of genes in each of the bacterial genomes enlisted in BGD arranged as per the order in terms of the genomic locations as listed in the said NCBI feature files (starting from the origin of replication) is termed as Bacterial Genome Map (BGM). BGM also contains information about functional annotations of each of these genes in the form of constituent protein domains identified in each gene. An example scenario of a sample BGM map shown below in Table 2.

TABLE 2

| Sr. No. | Genome ID | Organism name | Gene ID | Domains | Gene location |
|---------|-----------|---------------|---------|---------|---------------|
| 1 | Genome1/ Org1/S1 | Strain XXXX | Gene 1 | D1, D10, D11 | 12--112 |
| | | | Gene 2 | D2, D13 | 114--259 |
| | | | Gene 3 | D3, D14 | 312-555 |
| | | | . . . | | . . . |
| 2 | Genome2/ Org2/S2 | Strain YYYY | Gene 1 | D1 | 150--306 |
| | | | Gene 2 | D6, D15, D17 | 459--673 |
| | | | Gene 3 | D8, D18 | 682--1245 |
| | | | . . . | | . . . |
| 3 | Genome3/ Org3/S3 | Strain ZZZZ | Gene5 | D9 | 763--7998 |
| | | | Gene7 | D4, D19, D20 | 223--569 |
| . . . | . . . | . . . | . . . | | . . . |

Further, at step 310 of process 300, the processors 108 are configured to create a Metabolite Pathway-Domain Map (MPDM) for each of the plurality of skin metabolites based on the Mmap. The MPDM comprises all PiSM in Mmap and corresponding protein domains. An example scenario of a prototype for MPDM is provided in Table 3.

TABLE 3

| Sr. No. | Pathway | Metabolite | Domains |
|---------|---------|------------|---------|
| 1 | P1 | M1 | D1 |
| | | M3 | D2 |
| | | M9 | D3 |
| | | | . . . |
| 2 | P2 | M2 | D2 |
| | | | D5 |
| | | M5 | D9 |
| | | | . . . |

Further, at step 312 of the process 300, the processors 108 are configured to identify one or more protein domains in the MPDM which are present as gene clusters on a genome enlisted in the BGM. In an embodiment, each pathway is considered as the key found in the hash MPDM, the value corresponding to the key is a list of corresponding protein domains in the pathway. Genes belonging to a pathway often occur in proximity on their corresponding genomes and are termed as gene clusters. The distance on the genome in terms of the number of flanking genes within which the set of domains forming a pathway should lie in order to form a functional gene cluster varies and is often defined using manual and literature-based curation.

In an embodiment, the distance is defined as number of genes based on their genomic locations (termed as window size) within which the domains should lie in order to indicate a gene cluster and therefore indicate the pathway presence. Each protein domain (Pfams) corresponding to values in hash MPDM for each pathway used as a key is searched in the BGM to find if the protein domains comprising a metabolite biosynthesis/degradation pathway are present as gene clusters on each genome enlisted in BGM.

Further, at step 314 of the process 300, the processors 108 are configured to create a genome-metabolite-pathway map (GMP) comprising metabolic pathway corresponding to the identified protein domains and corresponding genomes. The GMP having values 0 or 1 based on a first predefined criterion. In an embodiment, the first predefined criterion is based on occurrence of the list of protein domains within a predefined window. Any set of domains are considered to form a gene cluster if they are located within a defined window size on the genome. Window size refers to the number of genes upstream and downstream of a domain known to be a part of a pathway within which all other domains of the pathway must lie in order to accurately annotate the gene cluster. In one embodiment, the first pre-defined criterion for the pre-defined window is defined as a window size of 20 genes upstream and downstream of a query protein domain (which refers to any one protein domain within a metabolic pathway) on the genome.

The gene name and Pfams database-based domain assignment is recorded for presence of other protein domains in a pathway within the window (20 in this case). Window size can be variable depending on various factors like the candidate pathways and the domains involved. Further, a pathway is considered to be present if the number of domains in the genome contributing to this pathway and occurring within the window size (e.g. if 20 genes is window size then +20 and −20 genes of the query protein domain) crosses a threshold value (variable for each pathway and obtained using literature mining and manual curation) which is the ratio corresponding to minimum number of domains whose presence is necessary to confirm existence of pathway out of the total number of domains assigned in the MPDM corresponding to this pathway.

In an embodiment, after identification of the list of biosynthetic-degradation pathway for the list of genomes from the BGM based on the first pre-defined threshold criterion, a multi-dimensional matrix is created with genome names as rows and pathway information for each metabolite as columns. This is called as the genome-metabolite-pathway map (GMP). The GMP map is given a value of either 0 or 1 for each metabolite and pathway based on a first predefined criterion. The first predefined criterion is for each pathway in a bacterial genome. In case of bacterial genomes where the number of domains corresponding to the pathway in MPDM either do not occur on the genome or the number found within the defined window size (20 in this case) does not cross the threshold value, a value of 0 is assigned corresponding to that genome and the pathway in GMP. In one embodiment, the window size can be 20 genes occurring consecutively on the microbial genome. If the number of pathway protein domains found on a genome are above the threshold value (defined for candidate pathway using literature mining and manual curation) and are present within the defined window size (20 genes in this case) on a microbial genome, a value of 1 is assigned for the corresponding genome and the pathway in matrix GMP. Window size can be variable depending on the system and the candidate pathway. An example scenario of prototypes for GMP are shown in Table 4.

TABLE 4

| Genome/Org/Strain | P1 | P2 | P3 | P4 | P5 | . . . |
|-------------------|----|----|----|----|----|-------|
| Genome1/Org1/S1 | 0 | 1 | 0 | 1 | 1 | . . . |
| Genome2/Org2/S2 | 1 | 0 | 0 | 1 | 1 | . . . |
| Genome3/Org3/S3 | 0 | 1 | 1 | 1 | 0 | . . . |
| Genome4/Org4/S4 | 1 | 0 | 0 | 0 | 1 | . . . |
| Genome5/Org5/S5 | 0 | 1 | 1 | 0 | 0 | . . . |
| . . . | . . . | . . . | . . . | . . . | . . . | . . . |

Further, at step 316 of the process 300, the processors 108 are configured to create a FGmap based on the GMP with genera and metabolic pathways, wherein the FGmap having values 0 or 1 based on a second predefined criterion and wherein the GMP and FGmap together form a knowledge base. In an embodiment, in cases where input taxonomic abundance is obtained at genus level, the GMP can be further processed to identify pathway composition at a genus level. The presence of a pathway in each strain belonging to a genus is analyzed. The pathway is considered to be present in a genus Ge if the ratio of number of strains of Genus Ge possessing a pathway out of the total sequenced strains belonging to a genus Ge in BGD is higher than the second pre-defined threshold criterion. The second pre-defined threshold criterion value is determined using manual interventions since number of strains sequenced for a genus may vary and the threshold needs to be decided accordingly.

In an embodiment, the second pre-defined threshold criterion is considered to be 0.7, wherein the pathway can be considered to be present in a genus Ge if 70% of strains of Genus Ge whose sequences are available in repositories contain the pathway. Different threshold values depending on manual analysis as well as literature mining can be decided and are within the scope of this disclosure. The genus-pathway binary matrix so obtained contains a value of 0 if a pathway is not found to occur in strains belonging to that genus above a threshold and value of 1 if the number of strains in which a pathway is found increases a threshold value. This matrix is termed as FGmap.

Further, at step 318 of the process 300, the processors 108 are configured to form the microbe-malodorant bacterial knowledge base by combining the FGmap and the genome-metabolite-pathway map (GMP) 110. An example scenario of prototypes for FGmap are shown in Table 5.

TABLE 5

| Genus | P1 | P2 | P3 | P4 | P5 | . . . |
|-------|----|----|----|----|----|-------|
| Genus 1 | 1 | 1 | 0 | 1 | 0 | . . . |
| Genus 2 | 1 | 0 | 1 | 0 | 1 | . . . |
| Genus 3 | 0 | 1 | 0 | 1 | 0 | . . . |
| Genus 4 | 1 | 1 | 1 | 0 | 1 | . . . |
| Genus 5 | 0 | 1 | 1 | 1 | 0 | . . . |
| . . . | . . . | . . . | . . . | . . . | . . . | . . . |

The embodiments of the present disclosure provides a mechanism or the solution to design the personalized composition for counteracting skin malodor of the subject, using the metabolite composition present in the biological sample of the subject. The designed personalized composition of the present disclosure has the metabolic capability to degrade the one or more identified malodorants and possess the capability of colonizing on skin of the subject, and hence the personalized composition is effective for counteracting or reducing the skin malodor of the subject. Further, the personalized compositions will not harm any useful skin microbes present in the subject.

The written description describes the subject matter herein to enable any person skilled in the art to make and use the embodiments. The scope of the subject matter embodiments is defined herein and may include other modifications that occur to those skilled in the art. Such other modifications are intended to be within the scope of the present disclosure if they have similar elements that do not differ from the literal language of the embodiments or if they include equivalent elements with insubstantial differences from the literal language of the embodiments described herein.

The embodiments of present disclosure herein addresses unresolved problem of treating skin malodor by designing the personalized compositions comprising bacteria that degrade malodorant on skin of an individual. The compositions may also comprise live bacterial strains which contain the genes/proteins/enzymes forming metabolic pathways which can degrade odorant compounds or metabolites.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A method for designing a personalized composition for counteracting skin malodor of a subject, comprising the steps of:

collecting a biological sample of the subject for whom the personalized composition for counteracting skin malodor is to be designed, wherein the biological sample is a skin sample;

determining a metabolite composition comprising one or more metabolites, from the biological sample, using one or more analytical techniques including a Polymerase Chain Reaction (PCR), a quantitative polymerase chain reaction (qPCR), pyrosequencing, Denaturing gradient gel electrophoresis (DGGE), Restriction Fragment Length Polymorphism, microarrays, or Mass spectroscopy;

identifying, via one or more hardware processors, one or more malodorants present in the biological sample based on the one or more metabolites present in the determined metabolite composition, wherein the one or more malodorants is valeric acid, isovaleric acid, acetic acid, propionic acid, hydrogen sulfide, ammonia, thio-alcohols, steroid compounds, and/or aldehydes;

identifying via the one or more hardware processors, a subset of pathways using a microbe-malodorant microbial knowledge base, that degrade the one or more identified malodorants;

identifying at least one microbe, via the one or more hardware processors, using the microbe-malodorant microbial knowledge base, that (i) have a metabolic capability to degrade the one or more identified malodorants, (ii) possess a capability of colonizing on the skin of the subject, and (iii) are not pathogenic to the subject, wherein the microbe-malodorant microbial knowledge base is created by:

identifying a plurality of skin metabolites (SM) implicated to be malodorant, from one or more knowledge sources, wherein the one or more knowledge sources are knowledge databases created using a querying technique over an existing literature of the plurality of skin metabolites and their capability as the one or more malodorants, wherein the existing literature includes a patent literature database and a non-patent literature database;

identifying one or more microbial metabolic pathways that have the capability to degrade at least one of the plurality of skin metabolites, using a literature mining technique, to obtain a plurality of metabolic pathways corresponding to the plurality of skin metabolites, wherein each metabolic pathway comprises genes or enzymes, and a series of chemical reactions for degrading the malodorant, wherein a query string is used as an input for metabolite to search against the non-patent literature database or pathway repositories or the patent literature database, wherein a result set obtained from the literature search in the non-patent literature database or the patent literature database provides a list of abstracts corresponding to each journal publication as an output along with a list of organisms;

creating a matrix metabolite map (Mmap) having information pertaining to each of the plurality of skin metabolites, the corresponding metabolic pathways, and a microbe in which the metabolic pathway is experimentally characterized;

generating a bacterial genome map (BGM) for each genome listed in a bacterial genome database, wherein the BGM comprises a list of genes for each genome listed in the bacterial genome database and functional annotations for each gene of the list of genes in a form of constituent protein domains identified in each gene, and wherein the list of genes for each genome are arranged as per an order in terms of genomic locations starting from origin of replication, wherein information for each genome pertaining to its translated protein sequences for each gene and its location on genomes is obtained from a National Centre of Biotechnology Information (NCBI) repository, wherein the bacterial genome database is a database of a bacteria for which the genomes are used in analysis, wherein the genomes are functionally annotated to identify the protein domains within each gene on the genome using a plurality of methods including a gene homology Hidden Markov Model based identification, Position Specific Scoring matrices (PSSM), wherein a protein domain family database comprising HMMs corresponding to all protein domains is obtained by using the Hidden Markov Model based identification;

creating a metabolite pathway-domain map (MPDM) for each of the plurality of skin metabolites using the matrix metabolite map (Mmap), wherein the metabolite pathway-domain map (MPDM) comprises each of the plurality of metabolic pathways associated with the plurality of skin metabolites and a corresponding protein domain;

identifying one or more protein domain out of the protein domains present in the metabolite pathway-domain map (MPDM), that are present as gene clusters on each genome listed in the bacterial genome map (BGM), wherein each metabolic pathway is considered as a key found in the MPDM and a value corresponding to the key is a list of corresponding protein domains in the metabolic pathway, wherein a distance defined as a number of genes based on their genomic locations in terms of a window size within which the protein domains lie in order to indicate a gene cluster and indicate presence of the metabolic pathway, wherein each protein domain corresponding to values in the MPDM for each metabolic pathway used as the key is searched in the BGM to find if the protein domains comprising the metabolite pathway are present as the gene clusters on each genome listed in the BGM;

creating a genome-metabolite-pathway map (GMP) using the metabolic pathway and corresponding genomes, wherein the GMP is a multi-dimensional matrix created with genome names as rows and pathway information for each metabolite as columns after identification of a list of degradation pathway for a list of genomes from the BGM based on a first pre-defined threshold criterion, wherein the GMP map have a value of either 0 or 1 for each metabolite and the metabolic pathway based on the first predefined threshold criterion which is for each pathway in a bacterial genome, wherein when a number of pathway protein domains corresponding to the metabolic pathway in the MPDM either do not occur on the genome or the number found within the window size does not cross a threshold value, then a value of 0 is assigned corresponding to that genome and the metabolic pathway in the GMP, wherein when the number of pathway protein domains found on the genome are above the threshold value and are present within the window size on a microbial genome, then a value of 1 is assigned for the corresponding genome and the metabolic pathway in the GMP;

creating a genus-pathway binary matrix (FGmap) based on the genome-metabolite-pathway map (GMP) with genera and metabolic pathways, wherein the FGmap is a matrix indicating a presence or absence of the metabolic pathways in bacterial genera, and the presence of a metabolic pathway in a genus is defined based on a predefined occurrence threshold across sequenced strains of the genus, wherein the predefined occurrence threshold is 70%, wherein the metabolic pathway is considered to be present in the genus if a ratio of a number of strains of the genus possessing the metabolic pathway out of a total sequenced strains belonging to the genus in the bacterial genome database is higher than the pre-defined occurrence threshold; and forming the microbe-malodorant microbial knowledge base by combining the FGmap and the genome-metabolite-pathway map (GMP);

genetically engineering one or more skin-colonizing microbes with the identified subset of pathways, to obtain at least one genetically engineered microbes;

creating a personalized composition for counteracting skin malodor of the subject from at least one of (i) the at least one identified microbe, (ii) the at least one genetically engineered microbe, and (iii) the at least one identified microbe and the at least one genetically engineered microbe, along with at least one of (i) one or more cosmetically or pharmaceutically acceptable carriers and (ii) one or more cosmetically or pharmaceutically acceptable excipients; and topically administering the created personalized composition on the skin of the subject for counteracting skin malodor.

2. The method of claim 1, wherein the created personalized composition for counteracting skin malodor of a subject, is in the form of a lotion, cream, ointment, aerosol spray, mist, oil, or gel.

* * * * *